United States Patent
Olds et al.

(10) Patent No.: US 10,368,720 B2
(45) Date of Patent: Aug. 6, 2019

(54) SYSTEM FOR STEREO RECONSTRUCTION FROM MONOSCOPIC ENDOSCOPE IMAGES

(71) Applicant: The Johns Hopkins University, Baltimore, MD (US)

(72) Inventors: Kevin C. Olds, Baltimore, MD (US); Tae Soo Kim, Baltimore, MD (US); Russell H. Taylor, Severna Park, MD (US); Austin Reiter, Annapolis, MD (US)

(73) Assignee: The Johns Hopkins University, Baltimore, MD (US)

( * ) Notice: Subject to any disclaimer, the term of this patent is extended or adjusted under 35 U.S.C. 154(b) by 413 days.

(21) Appl. No.: 14/548,948

(22) Filed: Nov. 20, 2014

(65) Prior Publication Data
US 2016/0143509 A1    May 26, 2016

(51) Int. Cl.
*A61B 1/04*     (2006.01)
*A61B 1/00*     (2006.01)
(Continued)

(52) U.S. Cl.
CPC ...... *A61B 1/00009* (2013.01); *A61B 1/00193* (2013.01); *A61B 1/05* (2013.01);
(Continued)

(58) Field of Classification Search
CPC .......... A61B 1/00193; A61B 2090/366; A61B 2090/367; A61B 1/00009; A61B 1/012;
(Continued)

(56) References Cited

U.S. PATENT DOCUMENTS

| 4,656,508 A | * | 4/1987 | Yokota | ............... G01B 11/2509 348/135 |
| 5,090,400 A | | 2/1992 | Saito | |

(Continued)

FOREIGN PATENT DOCUMENTS

WO     WO-2013/163391 A1    10/2013

OTHER PUBLICATIONS

Ackerman et al., "Real-time anatomical 3D image extraction for laparoscopic surgery." *Studies in health technology and informatics* (2001): 18-22.

(Continued)

*Primary Examiner* — Ryan N Henderson
*Assistant Examiner* — Pamela F Wu
(74) *Attorney, Agent, or Firm* — Venable LLP; Henry J. Daley

(57) ABSTRACT

A system for stereo reconstruction from a monoscopic endoscope includes an image pick-up element at a distal end thereof and a working channel defined by a body of the monoscopic endoscope. The system comprises a light patterning component configured to be disposed within the working channel such that a light emitting end of the light patterning component will be fixed with a defined relative distance from the distal end of the image pick-up element. The system also includes a data processor adapted to be in communication with the image pick-up element. The light patterning component forms a pattern of light that is projected onto a region of interest. The data processor receives an image signal of the region of interest that includes the pattern, and determines a distance from the endoscope to the region of interest based on the image signal and based on the defined relative distance.

19 Claims, 9 Drawing Sheets

(51) Int. Cl.
*A61B 1/05* (2006.01)
*A61B 1/06* (2006.01)
*A61B 1/07* (2006.01)

(52) U.S. Cl.
CPC ............ *A61B 1/063* (2013.01); *A61B 1/0638* (2013.01); *A61B 1/0684* (2013.01); *A61B 1/07* (2013.01)

(58) Field of Classification Search
CPC ......... A61B 1/063; A61B 1/0646; A61B 1/07; G02B 23/2415; G02B 23/2423; G02B 23/2461; G02B 23/26
USPC ........................................................ 600/111
See application file for complete search history.

(56) References Cited

U.S. PATENT DOCUMENTS

| | | | |
|---|---|---|---|
| 5,150,254 A * | 9/1992 | Saitou .................... | A61B 1/018 348/65 |
| 5,436,655 A | 7/1995 | Hiyama et al. | |
| 5,693,003 A | 12/1997 | Wolfelschneider et al. | |
| 6,503,195 B1 * | 1/2003 | Keller ................ | A61B 1/00163 348/45 |
| 7,079,666 B2 * | 7/2006 | Coulombe ........... | G06K 9/2036 348/136 |
| 7,385,708 B2 | 6/2008 | Ackerman et al. | |
| 7,728,868 B2 | 6/2010 | Razzaque et al. | |
| 8,103,331 B2 | 1/2012 | Hoyt et al. | |
| 2002/0082474 A1 | 6/2002 | Yamamoto | |
| 2009/0059827 A1 | 3/2009 | Liu et al. | |
| 2011/0230894 A1 | 9/2011 | Simaan et al. | |
| 2012/0130258 A1 | 5/2012 | Taylor et al. | |
| 2013/0038161 A1 | 2/2013 | Pan | |
| 2013/0044185 A1 * | 2/2013 | Krishnaswamy .... | A61B 5/7257 348/45 |
| 2013/0079711 A1 | 3/2013 | Nair et al. | |
| 2014/0071238 A1 * | 3/2014 | Mertens ................... | A61B 1/07 348/45 |
| 2014/0085421 A1 * | 3/2014 | Kuth .................. | A61B 1/00193 348/45 |

OTHER PUBLICATIONS

Albitar et al., "Robust Structured Light Coding for 3D Reconstruction." *ICCV.* 2007.
Chan et al., "Miniaturized three-dimensional endoscopic imaging system based on active stereovision." *Applied optics* 42.10 (2003): 1888-1898.
Jowett et al., "Airway luminal diameter and shape measurement by means of an intraluminal fiberoptic probe: a bench model." *Archives of Otolaryngology-Head & Neck Surgery* 134.6 (2008): 637-642.
Kaufman et al. "The three-dimensional "insect eye" laparoscopic imaging system-a prospective randomized study." *Gynecological Surgery* 4.1 (2007): 31-34.
Kawasaki et al., "Dynamic scene shape reconstruction using a single structured light pattern." *Computer Vision and Pattern Recognition, 2008. CVPR 2008. IEEE Conference on.* IEEE, 2008.
Lee et al. "A 3D IR camera with variable structured light for home service robots." *Proceedings of the 2005 IEEE International Conference on Robotics and Automation.*
Schmalz et al., "An endoscopic 3D scanner based on structured light." *Medical image analysis* 16.5 (2012): 1063-1072.
Wu, Chenyu. 3D Reconstruction of Anatomical Structures from Endoscopic Images. Diss. Drexel University, 2010.
Zhang et al., "3D vision inspection for internal surface based on circle structured light." *Sensors and Actuators A: Physical* 122.1 (2005): 68-75.

* cited by examiner

SYSTEM FOR STEREO RECONSTRUCTION FROM MONOSCOPIC ENDOSCOPE IMAGES

BACKGROUND

1. Technical Field

The field of the currently claimed embodiments of this invention relates to endoscopic imaging, and more particularly to stereo reconstruction from monoscopic endoscopic images.

2. Discussion of Related Art

Endoscopy is extremely common and is often used for diagnostic purposes through natural orifices (e.g. nose, throat, gastrointestinal tract). FIG. 1 illustrates the use of an intra-nasal laryngeal flexible endoscope. Most medical flexible endoscopes are monoscopic, and give the user no sense of depth perception. This presents challenges when the goal is to obtain accurate measurements of anatomical structures, such as the diameter of the airway or sinus passages, which are highly relevant for many clinical procedures. The current primary method used to measure the airway diameter is to invasively insert various sizes of endotracheal tubes into the throat and measure when the tube stops sealing correctly. This can be time consuming and can result in trauma to the soft tissues in the throat.

High quality modern flexible endoscopes such as distal-chip scopes may have a camera chip embedded in the end of the scope, as shown in FIG. 2. The camera chip 200 may provide superior image quality compared to fiber-optic scopes, and may also free up space in the scope shaft for an open lumen 202, also known as a working channel, through which instruments may be inserted. Diagnostic endoscopy in the clinic is far more frequent than any surgery, and precise 3-D measurements could significantly simplify and enhance many diagnostic tests such as measuring airway size. An inexpensive, simple, quick, and disposable solution is needed for performing stereo reconstruction from monoscopic endoscopic images.

SUMMARY

According to some embodiments of the present invention, a system for stereo reconstruction from a monoscopic endoscope is provided. The monoscopic endoscope comprising an image pick-up element at a distal end thereof and a working channel defined by a body of the monoscopic endoscope. The working channel provides a port at the distal end of the monoscopic endoscope. The system for stereo reconstruction comprises a light patterning component configured to be disposed within the working channel of the monoscopic endoscope such that a light emitting end of the light patterning component will be fixed with a defined relative distance from the distal end of the image pick-up element. The system for stereo reconstruction also includes a data processor adapted to be in communication with the image pick-up element. The light patterning component forms a pattern of light that is projected onto a region of interest. The data processor is configured to receive an image signal of the region of interest that includes the pattern, and determine a distance from the endoscope to the region of interest based on the image signal and based on the defined relative distance between the light emitting end of the light patterning component and the distal end of the image pick-up element.

According to some embodiments of the present invention, an endoscopic system for stereo reconstruction includes a monoscopic endoscope comprising an image pick-up element at a distal end thereof and a working channel defined by a body of the monoscopic endoscope so as to provide a port at the distal end of the monoscopic endoscope. The endoscopic system further includes a light patterning component configured to be disposed within the working channel of the monoscopic endoscope such that a light emitting end of the light patterning component will be fixed with a defined relative distance from the distal end of the image pick-up element. The endoscopic system further includes a data processor adapted to be in communication with the image pick-up element. The light patterning component forms a pattern of light that is projected onto a region of interest, and wherein the data processor is configured to receive an image signal of the region of interest that includes the pattern. The data processor is further configured to determine a distance from the endoscope to the region of interest based on the image signal and based on the defined relative distance between the light emitting end of the light patterning component and the distal end of the image pick-up element.

BRIEF DESCRIPTION OF THE DRAWINGS

Further objectives and advantages will become apparent from a consideration of the description, drawings, and examples.

DETAILED DESCRIPTION

Figure 1:
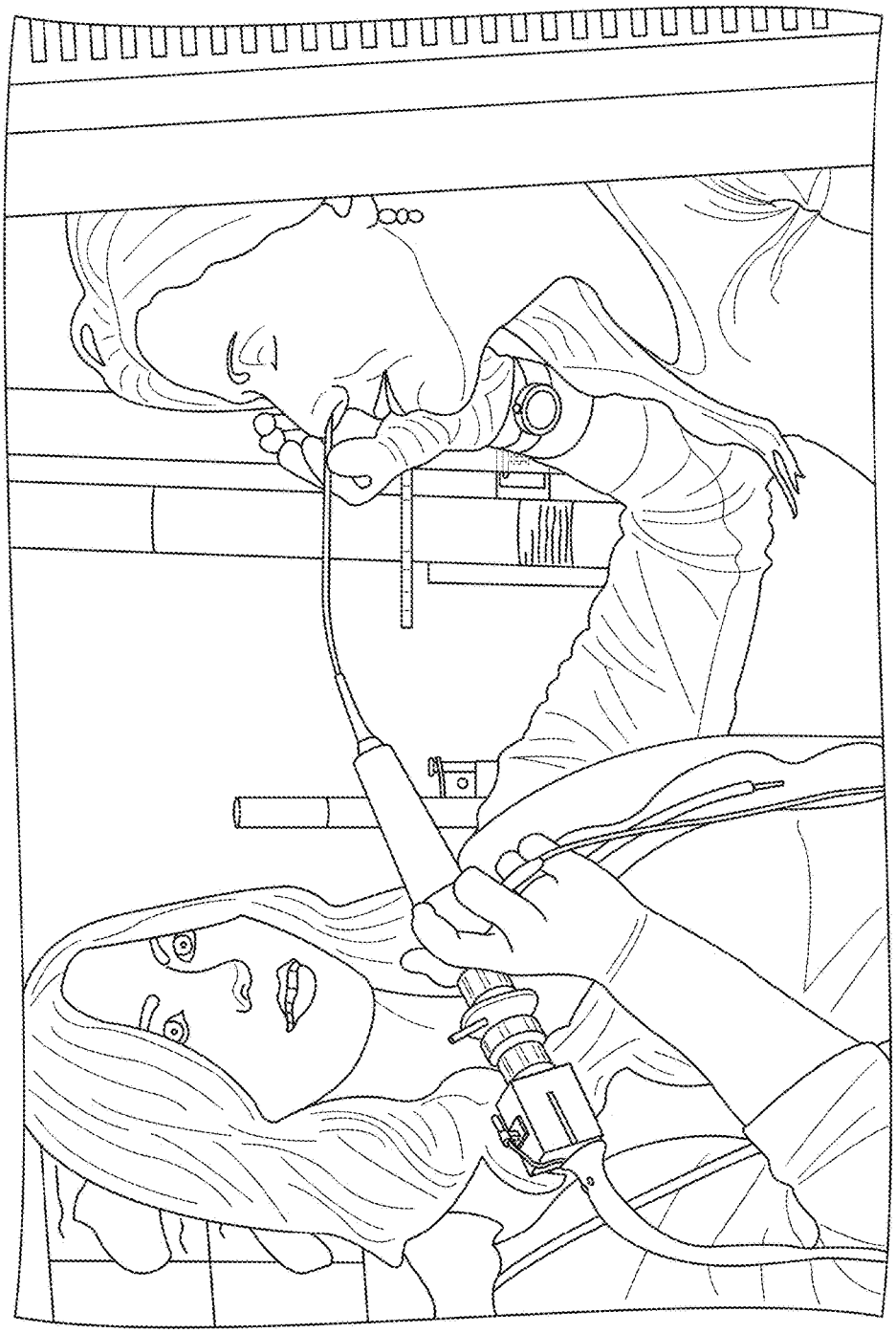
FIG. 1 shows an intra-nasal laryngeal flexible endoscope.
Figure 2:
FIG. 2 shows a modern distal chip flexible laryngeal endoscope with a working channel.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Ideally an endoscope would be capable of giving the physician a 3-D image which could be measured quantitatively to determine the size of anatomical structures, but the size and cost constraints of most flexible endoscopes prevent them from using two cameras to create a stereo baseline.

With rigid endoscopes, such as in laparoscopic surgery, stereo endoscopes are already in use, such as the Da Vinci Surgical System from Intuitive Surgical. Another approach taken in (Kaufman, Y., et al. "The three-dimensional "insect eye" laparoscopic imaging system-a prospective randomized study." *Gynecological Surgery* 4.1 (2007): 31-34) was to use a custom lens like an insect eye with multiple small lenses to provide different views, though this requires costly custom lens systems. Two camera flexible endoscopes have also been developed (Simaan, Xu, Goldman, Ding, Allen, Fowler. "Systems, devices, and method for providing insertable robotic sensory and manipulation platforms for single port surgery." U.S. patent application Ser. No. 13/063,615. 15 Apr. 2010). However, even with two or more cameras to create a stereo baseline, conventional stereo reconstruction methods tend to perform poorly in low-texture environments, which are common in medical imaging.

In addition, a time-of-flight distance measurement system has been integrated into an endoscope,[1] the phase shift of the light has been measured to obtain distance measurements,[2] and a diffraction grating with white light and a spectrometer has been used to triangulate 3-D positions.[3,4] Another approach is to use a 3-D camera system. Conventional 3-D cameras such as the Microsoft Kinect use a projector and a camera together to triangulate the 3-D distances of points. Approaches like this are called "structured light" systems since they work by projecting a pattern with a known structure onto the objects to be measured, and observing how the pattern is distorted by the objects.

The terms "optical" and "light" are intended to have a broad meaning to refer to both visible and non-visible regions of the electromagnetic spectrum. For example, ultraviolet, near infrared and infrared light are intended to be included within the broad scope of the current invention.

Significant literature exists on how to use structured light to perform 3-D reconstruction in a medical context,[5] especially with rigid endoscopes (Reiter, Allen. "Surgical structured light system." PCT Application Number PCT/US2013/038161. 31 Oct. 2013; Ackerman, Keller. "Methods and systems for laser based real-time structured light depth extraction." U.S. Pat. No. 7,385,708. 10 Jun. 2008; Ackerman, Jeremy D., Kurtis Keller, and Henry Fuchs. "Real-time anatomical 3D image extraction for laparoscopic surgery." *Studies in health technology and informatics* (2001): 18-22; Keller, Ackerman, Rosenthal, Fuchs, State. "Methods and systems for real-time structured light depth extraction and endoscope using real-time structured light depth extraction." U.S. Pat. No. 7,385,708. 7 Jan. 2003; Razzaque, Keller, State, Green, Ackerman. "System and method of providing real-time dynamic imagery of a medical procedure site using multiple modalities." U.S. Pat. No. 7,728,868. 1 Jun. 2010; Wu, Chenyu. 3*D Reconstruction of Anatomical Structures from Endoscopic Images*. Diss. Drexel University, 2010). The conventional approach is to use a projector and a camera together.[6] Another approach is to use a laser with an active pattern generator with a second optical channel in the scope.[7] The active pattern generator may include a mechanical component that moves to create a changing optical pattern, for example by moving a mirror. However, the active pattern generator may have a size constraint that prevents it from fitting in a conventional endoscope, and may raise issues of heat management, sterilizability/disposability, and safety. These methods require expensive equipment and/or highly customized endoscopes, limiting their practical use.

Additionally, methods using projectors to send patterns through rigid endoscopes are not applicable to modern distal chip flexible endoscopes since these scopes have no direct optical channel to transmit the pattern as rigid endoscopes do.

Another approach is to use motion of the light source illuminating the scene to create shading effects from which depth can be determined. This has been done in medical contexts such as (Hoyt, Domenicali. "Systems and methods for in-vivo optical imaging and measurement." U.S. Pat. No. 8,103,331. 24 Jan. 2012). However, this approach suffers from significant difficulties since light transmission and reflection properties of biological tissue are highly complex and variable.

Figure 3:
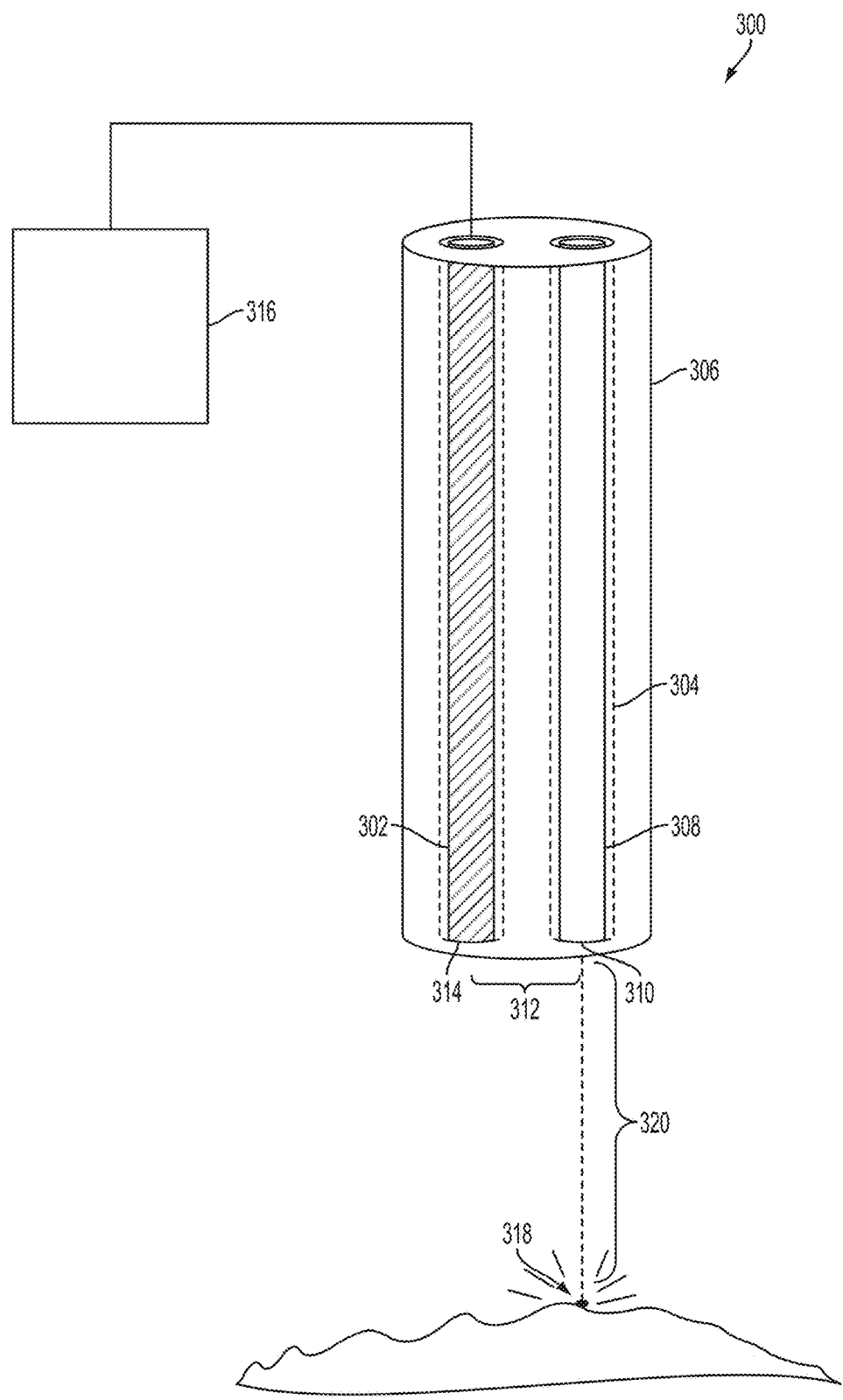
FIG. 3 shows a system for stereo reconstruction from a monoscopic endoscope.

FIG. 3 shows a system 300 for stereo reconstruction from a monoscopic endoscope. The monoscopic endoscope comprising an image pick-up element 302 at a distal end thereof and a working channel 304 defined by a body 306 of the monoscopic endoscope. The working channel 304 provides a port at the distal end of the monoscopic endoscope. The system 300 for stereo reconstruction comprises a light patterning component 308 configured to be disposed within the working channel 304 of the monoscopic endoscope such that a light emitting end 310 of the light patterning component 308 will be fixed with a defined relative distance 312 from the distal end 314 of the image pick-up element 302. The system 300 for stereo reconstruction also includes a data processor 316 adapted to be in communication with the image pick-up element 302. The light patterning component 308 forms a pattern of light 318 that is projected onto a region of interest. The data processor 316 is configured to receive an image signal of the region of interest that includes the pattern 318, and determine a distance 320 from the endoscope to the region of interest based on the image signal and based on the defined relative distance 312 between the light emitting end 310 of the light patterning component and the distal end 314 of the image pick-up element 302.

According to some embodiments of the invention, the light patterning component 308 may be used to create a structured light pattern for 3-D reconstruction. The light patterning component 308 can then be inserted into the working channel 304 of an endoscope and used to project a pattern 318 onto the endoscope's visual field. The distance 312 between the working channel and the endoscope camera is constant and known, forming a baseline for stereo reconstruction.

Figure 4:
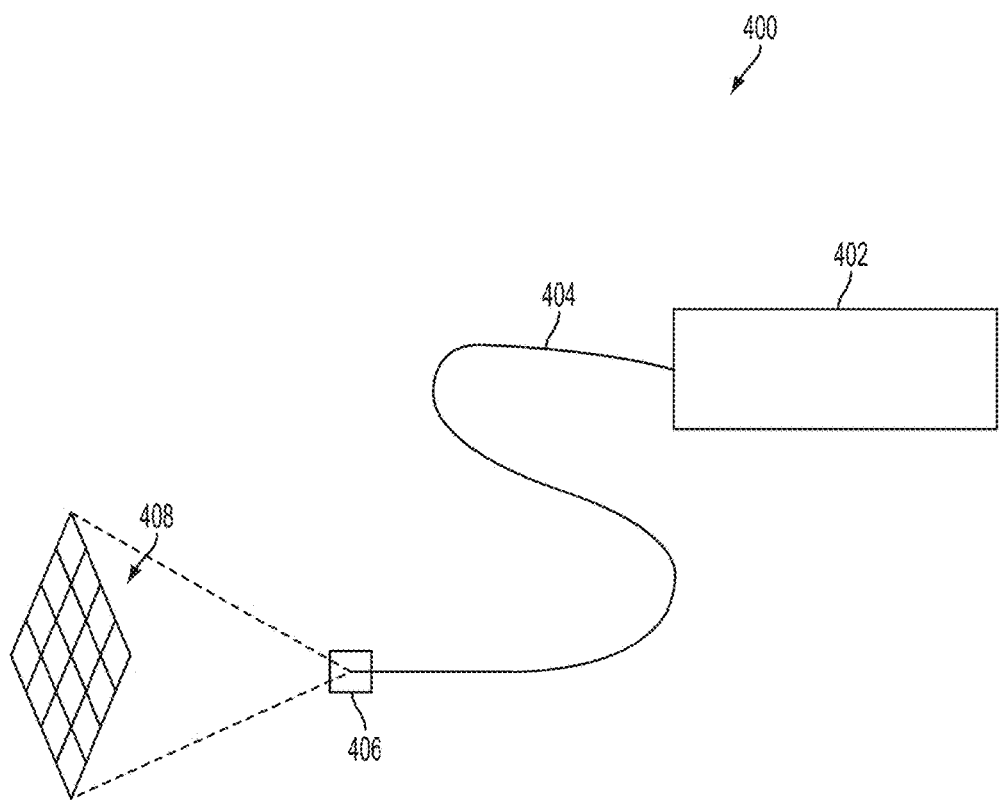
FIG. 4 shows a light patterning component comprising an illumination source, a transmission component, and a pattern formation component according to an embodiment of the invention.

An example of a light patterning component according to some embodiments of the invention is shown in FIG. 4. The light patterning component 400 includes an illumination source 402, a transmission component 404 having a first end axially aligned with the illumination source 402, and a pattern formation component 406 such as a lens or diffraction grating adhered to a second end of the transmission component 404. The transmission component 404 and the pattern formation component 406 are positioned parallel to an image pick-up element disposed within an endoscope body. The endoscope body may be a flexible endoscope body or a rigid endoscope body. The transmission component 404 may be an optical fiber, a fiber bundle, a wire, or any other type of component that transmits light and/or provides a physical connection between the illumination source 402 and the pattern formation component 406. According to some embodiments, the transmission component 404 transmits light from the illumination source 402, and the pattern formation component 406 forms a pattern 408 from the light which is projected onto a region of interest. The pattern enables a data processor to determine a distance from the endoscope body to the region of interest based on the pattern. The light patterning component is not limited to this configuration. Not all of the elements shown in FIG. 4 may be included, and other components and implementations may also be used.

Figure 5:
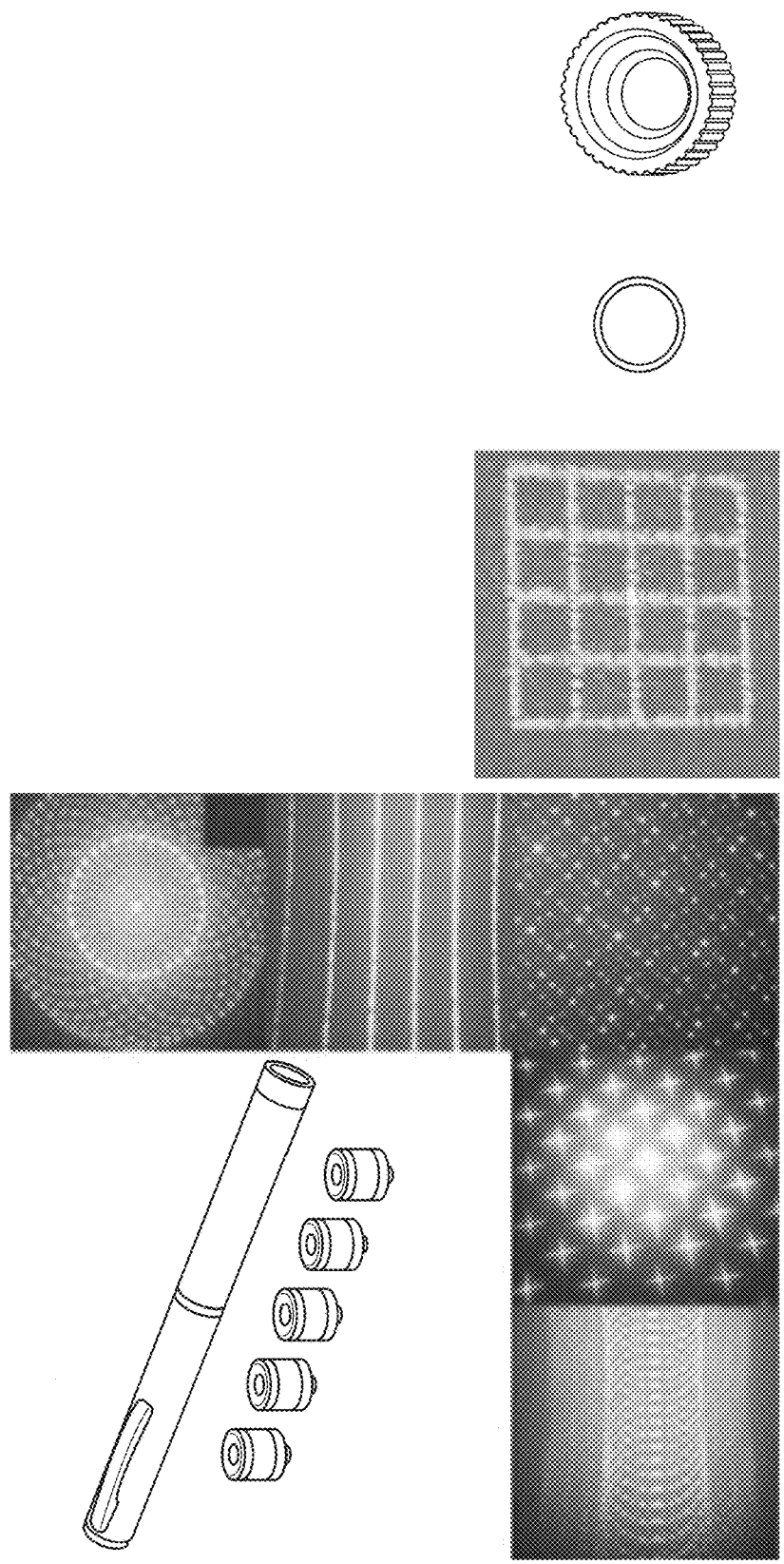
FIG. 5 shows a variety of patterns formed by a laser pointer and a number of diffraction gratings and lenses.

According to some embodiments of the invention, the illumination source may be a light emitting diode (LED), a projector, or a laser. Inexpensive laser pointers are capable of producing arbitrary static, monochromatic patterns of light when used with inexpensive diffraction gratings or lenses. FIG. 5 shows a variety of patterns formed by a laser pointer and a number of diffraction gratings and lenses. Similar gratings and lenses can be used according to some embodiments of the current invention. However, the general concepts of the current invention are not limited to these particular examples.

The pattern formation component 406 shown in FIG. 4 could be a separate component, or the transmission component 404, such as an optical fiber, for example, could have the pattern formation component 406 incorporated onto the end of it so that the light patterning component 308 shown in FIG. 3 could be fabricated as one component, reducing production costs. The illumination source 402 could be reusable, and could be external to the endoscope body 306 and even detachable from the transmission component 404. Alternatively, a small laser could be attached at the end of a flexible shaft, rather than using an external laser source with an optical fiber. Some commercial laser modules are as small as 3 mm in diameter and only cost a few dollars. These lasers typically run on less than 5 volts, and although the degree of electrical safety is not as high as in an endoscope that only contains optical components, it is still not difficult to make the optical illumination component safe. Based on the prices of commercial laser modules, it is possible that such a light patterning component could be made sufficiently inexpensively to be disposable.

Figure 6:
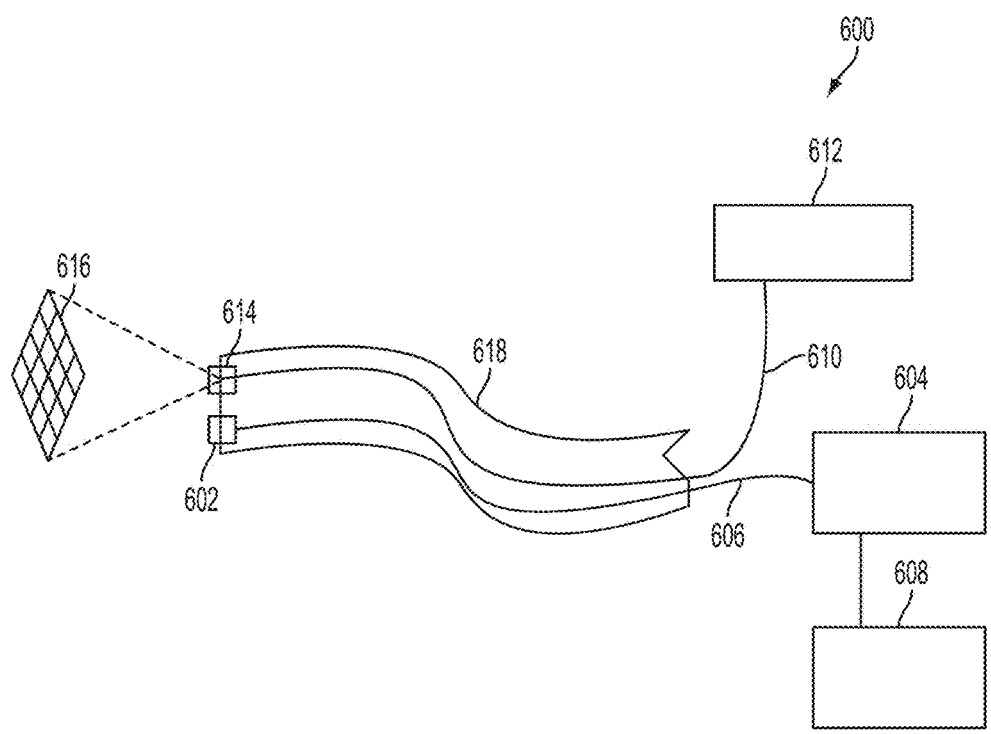
FIG. 6 is a schematic illustration of an endoscopic system for stereo reconstruction according to an embodiment of the invention.

FIG. 6 is a schematic illustration of an endoscopic system 600 for stereo reconstruction according to some embodiments of the invention. The endoscopic system 600 includes an endoscope camera 602 connected to a video processor 604 via a video transmission line 606. The video processor 604 may be in communication with a computer 608. The endoscopic system 600 further includes an optical fiber 610 to transmit light from a laser source 612 to a pattern formation component 614. The pattern formation component 614 may project a light pattern 616. The camera 602, video transmission line 606, optical fiber 610, and pattern formation component 614, may be at least partially disposed within and detachable from the endoscope body 618.

Two or more optical fibers having different patterning elements and transmitting different colors of laser light may be used to make patterns with multiple colors. Both fibers could be integrated together into a single insert to make insertion into the endoscope working channel easier. Alternatively, multiple lasers of different colors may be attached at the end of a flexible shaft and inserted into the endoscope working channel to generate patterns with multiple colors.

The system for stereo reconstruction shown in FIG. 3 includes a light patterning component and a data processor. These may be integrated into a conventional monoscopic endoscope to form a 3-D reconstruction endoscopic system. However, the light patterning component may not be required at all times, and accordingly the light patterning component may be provided separately from the monoscopic endoscope, to be inserted or attached when needed, and removed when not needed. Conventional, commercially available endoscopes can be retrofitted with the system for stereo reconstruction with without any modifications. The fibers, diffraction gratings, and lenses that may be included in the light patterning component can all be fabricated at very low cost, enabling them to be disposable. Different types of light patterns can be used, including but not limited to random patterns, a single line, multiple lines, a swept line, grids, points, arrangements of shapes, and a single point.

According to some embodiments of the invention, the light patterning component illustrated in FIG. 4 may include a projector 402, an optical fiber bundle 404, and a lens 406. The light from the projector 402 travels down the fiber bundle 404 and shines out through the lens 406 onto the visualization target. The projector 402 in this embodiment could consist of a laser or an LED source with a pattern generator, or a full video projector. If a full video projector is used, the system is able to project dynamic (time varying), full color patterns onto the visualization target. Using dynamic, full color patterns greatly increases the number and types of patterns, and allows for 3-D reconstruction algorithms to be used. Also, the projector can be computer controlled based on feedback from the image pick-up element, which enables even greater flexibility to dynamically adjust the pattern (color, shape, movement speed, etc.) to optimize the quality of the 3-D reconstruction. The optical illumination system may be a removable insert going through the working channel of the endoscope or attaching to the outside of the endoscope, or may be integrated directly into the scope. The endoscopic system could also be used to project patterns onto the object being viewed to convey information to the user. This information could be registered to the video image, providing an overlay on the object being viewed.

The projected pattern can provide at least the following two benefits. First, it can provide a stereo baseline so that the 3-D position of points on the pattern relative to the camera can be computed from monoscopic images. This can enable the creation of 3-D reconstructions with accurate absolute scale. Second, the projected pattern can provide a method of finding 3-D point locations even when there is no visible texture in the image itself. For example, if the camera is viewing a flat white plane like a piece of paper, there is no visible texture in the image, so no information about the 3-D locations of points on the paper can be determined. However, if a calibrated pattern is projected onto the paper, then the 3-D locations of the pattern points can all be calculated.

The system may use a combination of structured light methods and conventional image feature correspondence methods to create dense 3-D reconstructions. Although a single image with the pattern projected onto it would enable computation of 3-D positions of pattern points in that single image, the pattern points alone do not enable registration of this image to other images. In order to combine data from multiple images together into one 3-D model, corresponding features (such as Scale-Invariant Feature Transform (SIFT) features) would be found in the images and used to determine the spatial relationship between them up to scale, as is often done in Simultaneous Localization and Mapping (SLAM) methods. By combining these methods, a dense 3-D reconstruction can be formed from multiple images, even in low-texture environments with sparse features. In order to prevent the projected pattern from interfering with feature detection, it could be desirable to turn the pattern on and off as images are being acquired. The illumination source may be in communication with the data processor, and may turn on or off based on a command received from the data processor.

This system can also be integrated with robotic scope manipulation systems such as the Robo-ELF Scope disclosed in U.S. patent application Ser. No. 13/595,643 to further aid in scene reconstruction.

Figure 7:
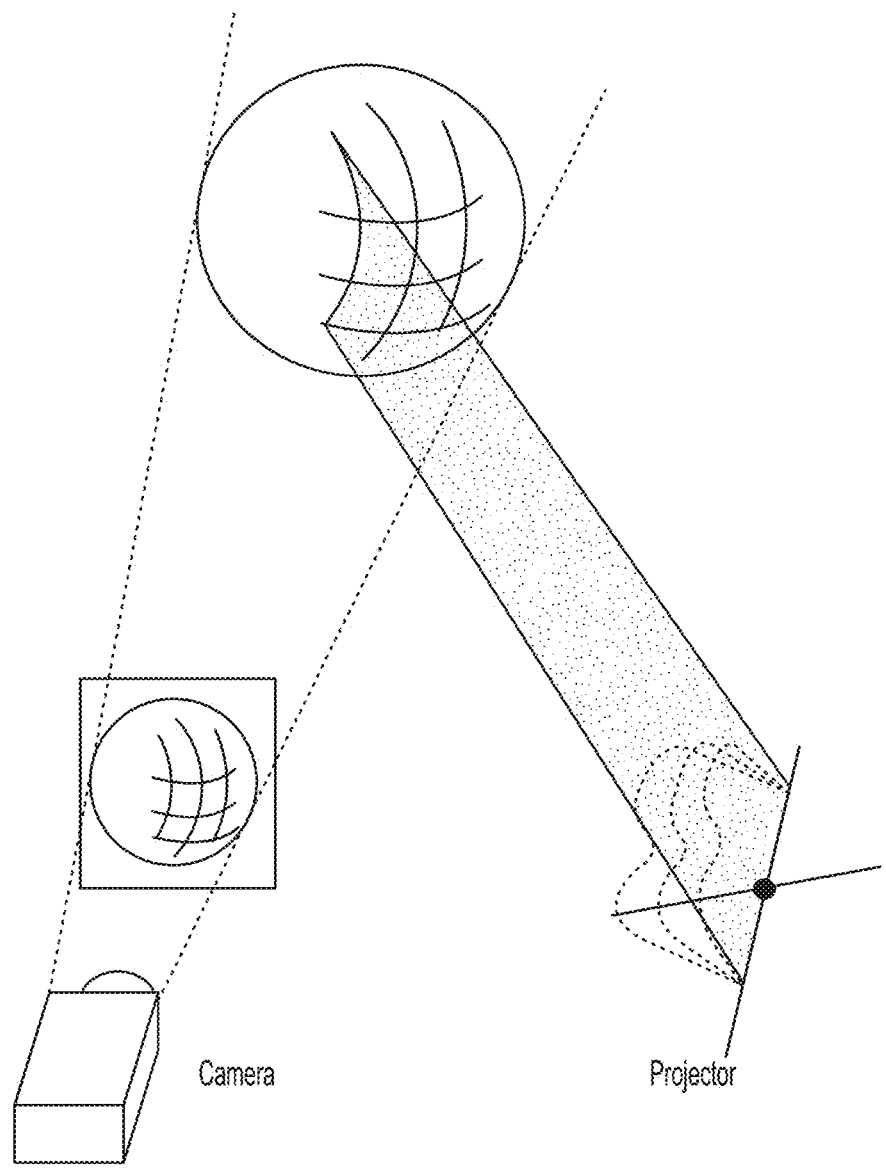
FIG. 7 is a schematic illustration of an approach of using structured light.

The endoscopic system and optical illumination system described herein may be used to project a single point onto the visual field of the image pick-up element. With calibration, this would enable the depth of a single point to be calculated in 3-D. This could be useful for estimating the depth and then the size of structures which are roughly coplanar with the camera plane. A grid pattern may be projected onto the visual field of the image pick-up element, such as a camera, and the algorithm from [8] may be used to compute the shape of the area of interest. This is illustrated in FIG. 7. The algorithm relies on having at least one distinctly recognizable point in the projection, so a bright point or one set of brighter horizontal and vertical lines could be incorporated to provide this. In order to distinguish the horizontal and vertical grid lines from each other, two fibers with independent lenses (one vertical, one horizontal) could be used with different color lasers (e.g., red and green) and incorporated into the same insert. A projection of a conventional structured light pattern involving arrangements of shapes, lines, or dots may enable the location of each part of the pattern to be determined based on local information in the projected image.[9]

The data processor may require calibration in order to determine the distance between the projecting end of the optical illumination component and the capturing end of the image pick-up element. The calibration may entail activating the pattern while the optical illumination component is situated in a lumen of the endoscope, and shining it on a calibration image such as a checkerboard. The image pick-up element captures an image of the pattern projected on the calibration image, and the data processor uses the captured image to determine the position of the projecting end of the optical illumination component with respect to the capturing end of the image pick-up element. The calibration process can be used to calibrate the camera itself, and to determine the relationship between the camera and the projected pattern. One way of doing this can be to use a checkerboard that can be printed so the size is known. The checkerboard can be shown to the camera from several different views to calibrate the camera. The projected pattern can then be turned on, and the camera can again view the checkerboard with the pattern from different angles, which allows the relationship between the pattern and the camera to be determined. The calibration process is independent of the type of projected pattern that is used.

Figure 8:
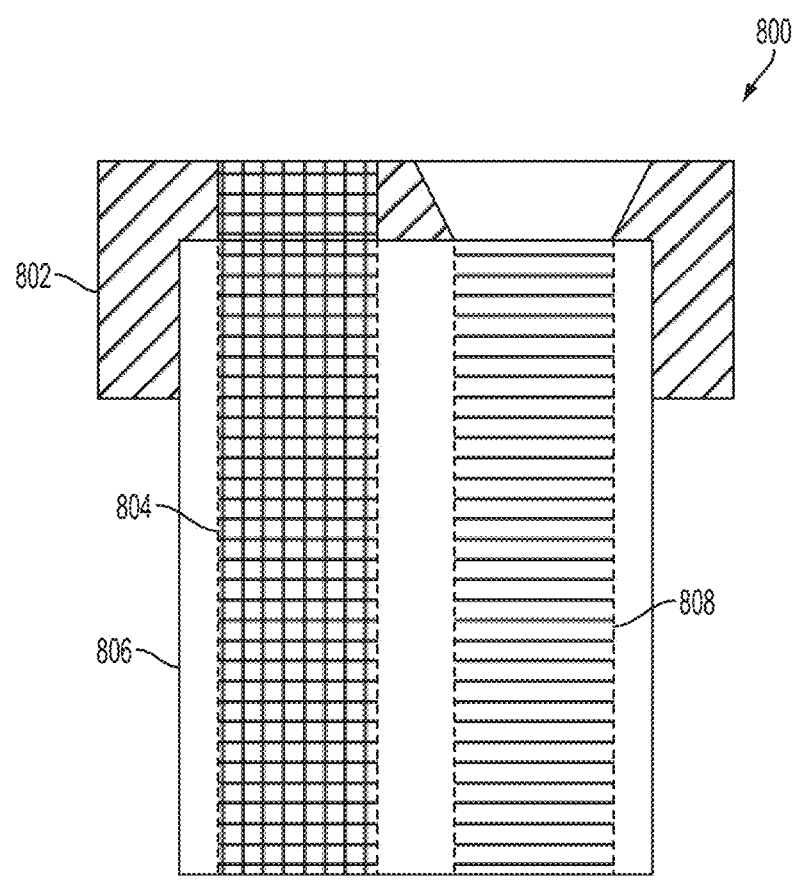
FIG. 8 shows an endoscopic system having an adapter according to some embodiments of the invention.
Figure 9:
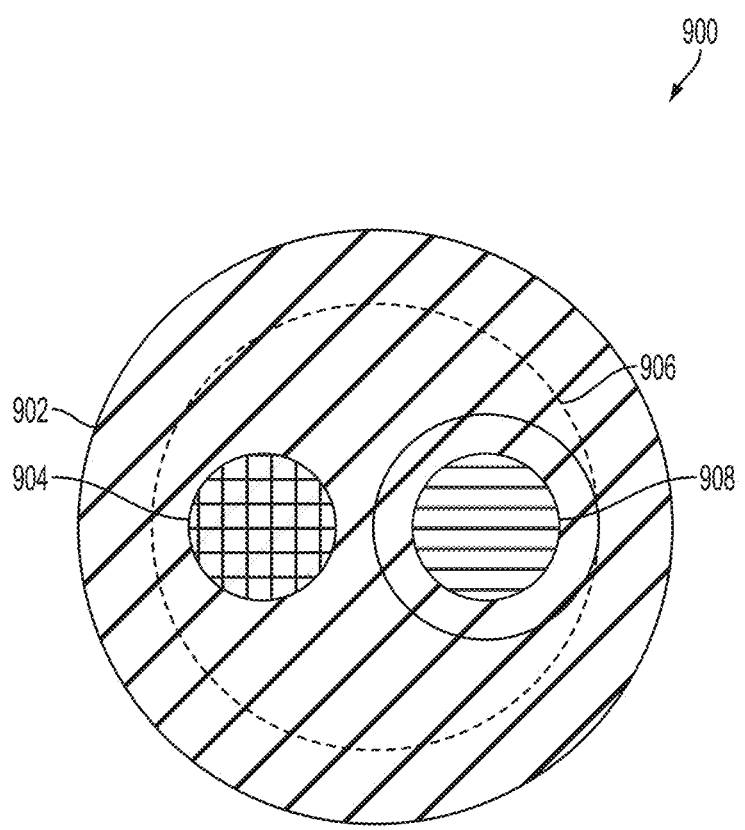
FIG. 9 shows from a different angle the endoscopic system having an adapter according to some embodiments of the invention.

In order for the calibration described herein to be reliable for extended operation of the endoscope without requiring recalibration, the end of the illumination component may be fixed with respect to the camera during operation. According to some embodiments of the invention an adapter is provided that attaches to the end of the endoscope and holds the illumination component in place. According to some embodiments of the invention the adapter fits on the outside of the distal end of the endoscope. FIG. 8 shows an endoscopic system 800 having an adapter 802. The light patterning component 804 extends beyond the end of the endoscope body 806 and fits into a hole or channel in the adapter 802. The adapter 802 includes a second hole or channel through which the image pick-up element captures the image of the sample. The adapter 802 keeps the position of the light patterning component 804 constant with respect to the image pick-up element 808. FIG. 9 shows the endoscopic system 900 from a different angle, with the adapter 902 fit on the end of the endoscope body 906, and the light patterning component 904 kept in constant position with respect to the image pick-up element 908. Once a single calibration is made with the light patterning component in this position, the endoscopic system can be repeatedly operated without the need for recalibration. Additionally, using the adapter, the light patterning component may be removed from the endoscope and later returned to its position within the endoscope without requiring recalibration. The adapter ensures that the position of the light patterning component remains constant.

According to some embodiments of the invention, the adapter and light patterning component are manufactured so that they are press-fit together, holding the adapter onto the end of the endoscope and holding the light patterning component within the adapter. Other methods for securing the adapter and light patterning component include the use of mechanical clamps, adhesives, and set screws. The adapter allows for the light patterning component to be used with a variety of existing, standard endoscopes. The endoscopes can be retrofitted with the light patterning component so that they can be used to perform accurate distance measurements in low-structure environments, and can create 3-D images of samples. The structured light component can be removed when it is not in use. If the light patterning component is disposed within a working channel of the endoscope, removal of the light patterning component allows for the working channel to be used for other purposes.

The endoscopic system and optical illumination system described herein allow for a light pattern to be projected onto an area of interest, and an image to be recorded. A surgeon may use the system during surgery to gain an understanding of the structure of the area of interest. However, the surgeon may not want the light pattern on the area of interest at all times, as it may obscure his or her view of the area of interest. Accordingly, the system may be configured such that the laser component of the optical system can be turned on briefly to illuminate the area of interest for the camera to capture the image, and then the laser component may be turned off. The laser source could also be computer controlled, so that it would only have to flash briefly to get an image for reconstruction. This is related to previous work on a multiplexed light source for retinal surgery disclosed in U.S. patent application Ser. No. 13/387,950, the entire contents of which are incorporated herein by reference.

If the endoscope is in motion, successive images should be close enough together in time to enable the 3-D reconstruction laser data and video data to be fused, enabling full color 3-D reconstructions. Techniques such as shape from shading and SLAM could also be combined with the structure light approach to further refine the 3-D reconstruction.

Even in stereo endoscopes that use two cameras, a structured light system could still be useful. Stereo vision systems typically work by detecting corresponding features in the two images. However, in many medical applications such as in the airway, the images do not contain many useful features. This results in sparse 3-D reconstruction of limited use. With a structured light pattern such as a grid projected onto the scene, depth information can be determined even for areas with no features, thus enabling a dense reconstruction.

Rather than passing through the lumen of a scope, the optical fiber and patterning means could be attached to the outside of the scope. Also, most scopes currently in clinics used for diagnosis do not have open lumens, so this would enable the system to be used with these scopes as well.

Instead of using a laser as the light source with a diffraction grating or lens at the end of the fiber, an LED could be used as the light source with a transparent plate with an opaque pattern on the end of the fiber. This would project a pattern using the difference between the transparent areas of the plate which allow light to shine through, and opaque areas of the pattern which create a shadow.

REFERENCES

1. Yamamoto, Kiyoshi. "Electronic endoscope with three-dimensional image capturing device." U.S. Patent Publication No. 2002/0082474 A1. 27 Jun. 2002.
2. Schmidtke, Gerhard, Peter Wilhelm, and Harald Wolfelschneider. "Endoscope and method for determining object distances." U.S. Pat. No. 5,693,003. 2 Dec. 1997.
3. Saito, Satoshi. "Measuring endoscope." U.S. Pat. No. 5,090,400. 25 Feb. 1992.
4. Jowett, Nathan, et al. "Airway luminal diameter and shape measurement by means of an intraluminal fiberoptic probe: a bench model." Archives of Otolaryngology—Head & Neck Surgery 134.6 (2008): 637-642.
5. Wu, Chenyu. 3D Reconstruction of Anatomical Structures from Endoscopic Images. Diss. Drexel University, 2010.
6. Keller, Kurtis P., et al. "Methods and systems for real-time structured light depth extraction and endoscope using real-time structured light depth extraction." U.S. Pat. No. 6,503,195. 7 Jan. 2003.
7. Ackerman, Jeremy D., and Kurtis P. Keller. "Methods and systems for laser based real-time structured light depth extraction." U.S. Pat. No. 7,385,708. 10 Jun. 2008.
8. Kawasaki, Hiroshi, et al. "Dynamic scene shape reconstruction using a single structured light pattern." Computer Vision and Pattern Recognition, 2008. CVPR 2008. IEEE Conference on. IEEE, 2008.
9. Albitar, Chadi, Pierre Graebling, and Christophe Doignon. "Robust Structured Light Coding for 3D Reconstruction." ICCV. 2007.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A system for stereo reconstruction from a monoscopic endoscope, said monoscopic endoscope comprising an image pick-up element at a distal end thereof and a working channel within a body of said monoscopic endoscope so as to provide a port at said distal end of said monoscopic endoscope, said system for stereo reconstruction comprising:
   a first illumination source and a second illumination source being configured to emit light of different colors;
   a light patterning component configured to be disposed within said working channel of said monoscopic endoscope such that a light emitting end of said light patterning component will be fixed with a defined relative distance from said distal end of said monoscopic endoscope, said light patterning component being further configured to receive the light of different colors at a proximal end of said monoscopic endoscope; and
   a data processor adapted to be in communication with said image pick-up element,
   wherein the first illumination source is configured to emit a first plurality of lines extending in a first direction and the second illumination source is configured to emit a second plurality of lines extending in a second direction different from said first direction,
   wherein said first plurality of lines and said second plurality of lines are of said different colors,
   wherein said first plurality of lines and said second plurality of lines together form a pattern of light in a shape of a grid that is projected onto a region of interest,
   wherein said data processor is configured to receive an image signal of said region of interest that includes said pattern, and
   wherein said data processor is further configured to determine a distance from said monoscopic endoscope to said region of interest based on said image signal and based on said defined relative distance between said light emitting end of said light patterning component and said distal end of said image pick-up element.

2. The system for stereo reconstruction from a monoscopic endoscope according to claim 1, wherein said data processor is configured to construct a three-dimensional image of said region of interest based on said image signal and based on said defined relative distance between said light emitting end of said light patterning component and said distal end of said image pick-up element.

3. The system for stereo reconstruction from a monoscopic endoscope according to claim 1, wherein said pattern comprises at least one dot.

4. The system for stereo reconstruction from a monoscopic endoscope according to claim 1, wherein said pattern further includes a swept line.

5. The system for stereo reconstruction from a monoscopic endoscope according to claim 1, wherein said light patterning component is configured to emit light upon receipt of a command from said data processor.

6. The system for stereo reconstruction from a monoscopic endoscope according to claim 1, wherein said first illumination source is a laser.

7. The system for stereo reconstruction from a monoscopic endoscope according to claim 1, wherein said first illumination source is a light emitting diode (LED).

8. The system for stereo reconstruction from a monoscopic endoscope according to claim 1, wherein said first illumination source is a projector.

9. The system for stereo reconstruction from a monoscopic endoscope according to claim 1, wherein said first illumination source is external to said working channel.

10. The system for stereo reconstruction from a monoscopic endoscope according to claim 1, wherein the light patterning component further comprises a first transmission component and a second transmission component, said first transmission component having a first end axially aligned with said first illumination source and said second transmission component having a first end axially aligned with said second illumination source, wherein said first transmission component transmits light from said first illumination source and said second transmission component transmits light from said second illumination source.

11. The system for stereo reconstruction from a monoscopic endoscope according to claim 10, wherein said first transmission component is an optical fiber.

12. The system for stereo reconstruction from a monoscopic endoscope according to claim 10, wherein said first transmission component is an optical fiber bundle.

13. The system for stereo reconstruction from a monoscopic endoscope according to claim 10, further comprising a lens adhered to a second end of said first transmission component.

14. The system for stereo reconstruction from a monoscopic endoscope according to claim 10, further comprising a diffraction grating adhered to a second end of said first transmission component.

15. The system for stereo reconstruction from a monoscopic endoscope according to claim 10, further comprising a transparent plate with an opaque pattern on said transparent plate adhered to a second end of said first transmission component.

16. The system for stereo reconstruction from a monoscopic endoscope according to claim 1, further comprising:
  an adapter disposed around a distal end of said monoscopic endoscope and defining a first channel for receiving said light patterning component and a second channel enabling said image pick-up element to capture an image.

17. The system for stereo reconstruction from a monoscopic endoscope according to claim 1, wherein said light patterning component is configured to be attached to and detached from said monoscopic endoscope, and wherein said monoscopic endoscope is a conventional monoscopic endoscope.

18. An endoscopic system for stereo reconstruction, comprising:
  a monoscopic endoscope comprising an image pick-up element at a distal end thereof and a working channel within a body of said monoscopic endoscope so as to provide a port at said distal end of said monoscopic endoscope;
  a first illumination source and a second illumination source being configured to emit light of different colors;
  a light patterning component configured to be disposed within said working channel of said monoscopic endoscope such that a light emitting end of said light patterning component will be fixed with a defined relative distance from said distal end of said monoscopic endoscope, said light patterning component being further configured to receive the light of different colors at a proximal end of said monoscopic endoscope; and
  a data processor adapted to be in communication with said image pick-up element,
  wherein the first illumination source is configured to emit a first plurality of lines extending in a first direction and the second illumination source is configured to emit a second plurality of lines extending in a second direction different from said first direction,
  wherein said first plurality of lines and said second plurality of lines are of different colors,
  wherein said first plurality of lines and said second plurality of lines together form a pattern of light in a shape of a grid that is projected onto a region of interest,
  wherein said data processor is configured to receive an image signal of said region of interest that includes said pattern, and
  wherein said data processor is further configured to determine a distance from said monoscopic endoscope to said region of interest based on said image signal and based on said defined relative distance between said light emitting end of said light patterning component and said distal end of said image pick-up element.

19. The endoscopic system for stereo reconstruction according to claim 18, wherein said monoscopic endoscope includes said image pick-up element, and wherein said light patterning component is configured to fit at least partially into said monoscopic endoscope.

* * * * *